United States Patent [19]

Frushour

[11] 4,364,675

[45] Dec. 21, 1982

[54] WET MELTING POINT ANALYSIS

[75] Inventor: Bruce G. Frushour, Cary, N.C.

[73] Assignee: Monsanto Company, St. Louis, Mo.

[21] Appl. No.: 246,489

[22] Filed: Mar. 23, 1981

[51] Int. Cl.$^3$ .......................................... G01N 25/04
[52] U.S. Cl. ...................................... 374/16; 374/10; 526/330; 526/342
[58] Field of Search ............ 73/15 B, 17 R; 526/330, 526/342

[56] References Cited

U.S. PATENT DOCUMENTS 3,468,840  9/1969  Heiberger et al. .............. 526/330 X

OTHER PUBLICATIONS

Thermal Analysis Bulletin by Dupont #900A-1, 2-8-66.
Slade, P. E., *Thermochim. Acta*, 1 (1970) pp. 459-463.

*Primary Examiner*—Herbert Goldstein
*Attorney, Agent, or Firm*—John W. Whisler

[57] ABSTRACT

A method for determining the amount of copolymerized vinyl monomer in a acrylonitrile/vinyl monomer copolymer is provided. The method is based on the fact that increasing the vinyl monomer content of the copolymer reduces its melting point. The method consists of first determining the melting point of the copolymer while the copolymer is saturated with water. The presence of water reduces the melting point to a temperature below the range where thermal degradation of the copolymer occurs. The amount of copolymerized vinyl monomer in the copolymer can then be determined by comparing its melting point in the presence of water to that of corresponding copolymers in which the vinyl monomer content thereof is known and varies from copolymer to copolymer.

4 Claims, No Drawings

4,364,675

WET MELTING POINT ANALYSIS

BACKGROUND OF THE INVENTION (a) Field of the Invention

This invention relates to a method for determining the amount of copolymerized vinyl monomer in a copolymer formed by copolymerizing acrylonitrile and a vinyl monomer. Acrylonitrile copolymers of this type which contain from 0 to 25% by weight of the vinyl monomer are referred to hereinafter as "acrylonitrile/vinyl monomer copolymers" or simply "A/V copolymers".

(b) Description of the Prior Art

Acrylic textile fibers prepared from A/V copolymers are widely used to provide apparel and homefurnishing fabrics. The dyeing properties of these acrylic fibers are dependent on the level of copolymerized vinyl monomer in the fiber, that is, variations in the level of copolymerized vinyl monomer in the fiber leads to variations in the annealing shrinkage of the fiber which in turn causes variations in the rate at which basic dye will diffuse into the fiber. Accordingly, to achieve fabrics having good dye uniformity characteristics the level of copolymerized vinyl monomer in the fibers from which the fabrics are constructed must be controlled within a narrow range which in turn requires a good analytical method for measuring the level of copolymerized vinyl monomer in the fiber or the copolymer from which the fiber is formed.

Present analytical methods (e.g., infrared methods) used to measure the level of copolymerized vinyl monomer in A/V copolymers involve rather complicated procedures and provide only a mediocre degree of accuracy. Accordingly, there is a need in the art to provide a simple method by which the level of copolymerized vinyl monomer can be more accurately measured, thereby enabling fibers and fabrics of improved dye uniformity to be obtained. The main object of the present invention is to provide such a method.

SUMMARY OF THE INVENTION

In accordance with the present invention, a simple method is provide for accurately determining the amount of copolymerized vinyl monomer in an acrylonitrile/vinyl monomer copolymer of the type formed by copolymerizing acrylonitrile and a vinyl monomer, comprising:

(1) mixing sufficient water with said acrylonitrile copolymer to provide a homogeneous mixture of copolymer and water in which the copolymer is saturated with water (2) increasing the temperature of the mixture under conditions whereby the copolymer remains saturated with water and noting the temperature at which the copolymer melts under said conditions, and (3) from melting point/composition data previously obtained and compiled for a series of acrylonitrile/vinyl monomer copolymers of known composition and formed from the same vinyl monomer wherein the amount of vinyl monomer varied from copolymer to copolymer and melting points were determined in the manner set forth in above steps (1) and (2), translate the melting point obtained in step (2) to % by weight copolymerized vinyl monomer.

The previously obtained data, for example, may be compiled in the form of a curve obtained from standards (i.e., samples of the same acrylonitrile/vinyl monomer copolymer as the copolymer being analyzed where the amount of the monomers is known and varied from sample to sample) by plotting the melting point against the amount of vinyl monomer of the copolymer or in the form of an equation defining such a curve.

The method of this invention is useful in determining vinyl monomer levels in A/V copolymers containing up to about 25% by weight vinyl monomer. When the vinyl monomer level exceeds about 25% by weight, a melting point endotherm can no longer be observed.

The addition of water to an A/V copolymer reduces the melting point of the copolymer so that it melts without significant degradation. The melting point of the copolymer in the presence of water decreases as the water content of the copolymer/water mixture is increased until the copolymer becomes saturated with water at which point a minimum melting point is reached. Thereafter, increasing the water content has no further effect on the melting point of the copolymer component of the mixture because the additional water merely forms a second phase. Preferably, sufficient water is added to the test copolymer to saturate the copolymer with water and provide the minimum melting point, otherwise, the previously obtained data must be obtained from mixtures (i.e., standards) all having the same water content as the test sample.

The method of the present invention is particularly useful as an analytical tool for controlling the amount of copolymerized vinyl monomer in fibers produced from A/V copolymers. Such copolymers include, but are not limited to, copolymers formed by copolymerizing acrylonitrile with one of the following vinyl monomers: vinyl acetate, vinyl chloride, vinylpyridine, methyl methacrylate, methacrylate, alkyl vinyl ethers, styrene and vinylidene chloride.

DESCRIPTION OF THE PREFERRED EMBODIMENTS

In practicing the method of the present invention, the melting point of the A/V copolymer component of the copolymer/water mixture is conveniently determined using a differential scanning calorimeter, such as Perkin-Elmer Model DSC-2, equipped to printout a melting endotherm curve. The melting point corresponds to the peak temperature of the endotherm curve. The mixture is sealed from the atmosphere in a high-pressure capsule provided for this purpose. The capsule is then placed in the calorimeter and heated at a given rate.

In preparing the copolymer/water mixtures for melting point determination, preferably, sufficient water is added to assure that the copolymers will remain saturated with water during test and, thereby melt at their minimum melting points.

Although the experiments described in the examples to follow were carried on fiber-forming acrylonitrile/vinyl acetate copolymers (hereinafter referred to as An/VA copolymers), other acrylonitrile/vinyl monomers will give similar results. In the case of AN/VA copolymers containing about 7.84% VA, the melting point decreases from 277° C. to 155° C. when the amount of water is increased from 0 to 13% by weight, based on the weight of the mixture. The addition of further water has no effect on the melting point. All AN/VA copolymers containing 25% by weight or less of VA will melt at their minimum melting point temperature if the mixture contains at least 25% by weight of water.

The method of the invention may be used to determine the vinyl monomer content of a shaped article, such as fibers. In such a case, the article is prepared for testing by first boiling it in water for a period of time (e.g., one hour) to remove any impurities present in the article such as residual spinning solvent. The article is then placed in the calorimeter and analyzed in the same manner as freshly prepared copolymer, except that it is first melted and then solidified in the calorimeter before actually measuring its melting point to remove any effects on melting point that may arise from the thermal history of the article.

The following examples are given to further illustrate the invention. In the examples percent is by weight unless otherwise specified.

EXAMPLE 1

The minimum melting point of nine AN/VA copolymers of known composition (standards) in which the percent copolymerized VA content ranged from a low of about 5.4% to a high of about 8.0% was determined using a Perkin-Elmer differential scanning calorimeter model DSC-2. In determining the melting points 10 grams of each copolymer was thoroughly mixed with 15 ml. of deionized water to obtain copolymer/water mixture which is in the form of a paste of convenient consistency for handling. Seventy-two grams of each mixture was enclosed in a Perkin-Elmer high-pressure, large-volume capsule (Part No. 319-0218) and the sample crimped. The crimped samples were placed in the DSC-2 sample pan which had been preheated to 80° C. After allowing two to three minutes for the samples to reach 80° C., the temperature of the sample pan was increased at the rate of 5° C. per minute and the chart speed set at 40 mm per minute. As the melting point of the copolymer was approached, the curved printed on the chart rose. At the melting point the curve peaked and thereafter fell as the temperature was increased. (The melting endotherm curve obtained was typical for crystalline polymer.) A perpendicular line was drawn from the peak to the temperature axis of the chart. The point at which this line crossed the temperature axis identified the temperature at which the copolymer melted. The following values were obtained.

| Sample | % VA | C-14-54-8010 Melting Point, °C. |
|---|---|---|
| 1 | 5.37 | 166.0 |
| 2 | 6.36 | 161.5 |
| 3 | 7.03 | 158.6 |
| 4 | 7.08 | 158.6 |
| 5 | 7.12 | 158.2 |
| 6 | 7.25 | 157.6 |
| 7 | 7.33 | 157.4 |
| 8 | 8.06 | 154.2 |
| 9 | 8.60 | 151.4 |

A straight line was obtained by plotting % VA against melting point for each of the above samples. The resulting plot provided a standard curve for AN/VA copolymers.

EXAMPLE 2

An AN/VA copolymer of unknown composition was analyzed using the apparatus and procedure described in Example 1. From its melting endotherm curve, the copolymer was determined to have a melting point of 157°. Using the standard curve obtained in Example 1, the copolymer was determined to have a copolymerized vinyl acetate level of 7.4%.

EXAMPLE 3

A curve was prepared for AN/VA copolymer fibers using the apparatus and technique described in Example 1 except in this instance the fiber samples were each boiled in deionized water for one hour to remove any residual dimethylacetamide that may not have been completely removed during fiber spinning and then, twenty mgs of the fiber was enclosed in the sample capsule and initially heated to 175° C. at the rate of 20° C./min. to melt the fiber and then cooled to 80° C. at the same ratio to remove the effects of processing (thermal history). The once-melted fiber samples were then treated as described in Example 1. The following values were obtained for the fiber samples:

| Sample | % VA | C-14-54-8010 Melting Point, °C. |
|---|---|---|
| 1 | 8.70 | 151.6 |
| 2 | 7.25 | 158.2 |
| 3 | 7.12 | 159.0 |

EXAMPLE 4

An AN/VA Copolymer fiber of unknown composition was analyzed using the apparatus and procedure of Example 1, modified as described in Example 3. From the melting point endotherm curve, the fiber was determined to have a melting point of 154.5° C. Using the curve obtained in Example 3, the fiber was determined to have a copolymerized vinyl acetate content of 8.0%.

Many small computers are availaable, that will accept the output of a differential scanning calorimeter and determine the derivative of the endotherm curve as a function of temperature. The temperature at which the derivative becomes zero corresponds to the endotherm peak temperature or melting point. The computer can be programmed to perform the desired calculations from standard and display the percent vinyl acetate of the sample being analyzed.

Other acrylonitrile copolymers which have been successfully analyzed for copolymerized vinyl monomer content in accordance with the method of this invention copolymers in which the vinyl monomer is vinyl chloride, vinylidene chloride, ethyl vinyl ether, methyl vinyl ether, methacrylate and styrene.

In carrying out the method of the invention it is important that all melting points are measured under the same conditions so as to minimize errors. The melting point of the copolymer observed from the endotherm chart may not be its actual melting point but may reflect thermal lag. However, correction for thermal lag is not necessary since it will be a constant for all of the samples.

I claim:
1. A method for determining the amount of copolymerized vinyl monomer in an acrylonitrile copolymer formed by copolymerizing acrylonitrile and a vinyl monomer, wherein said copolymer contains at least 75% by weight of acrylonitrile, comprising:
   (1) mixing sufficient water with said acrylonitrile copolymer to provide a homogeneous mixture of copolymer and water in which the copolymer is saturated with water,

(2) increasing the temperature of said mixture under conditions whereby the copolymer remains saturated with water and noting the temperature at which the copolymer melts under said conditions, and (3) from melting point/composition data previously obtained and compiled for a series of acrylonitrile/vinyl monomer copolymers of known composition and formed from the same vinyl monomer wherein the amount of vinyl monomer varied from copolymer to copolymer and melting points were determined in the manner set forth in above steps (1) and (2), translate the melting point obtained in step (2) to percent by weight copolymerized vinyl monomer.

2. The method of claim 1 wherein the vinyl monomer is vinyl acetate.

3. The method of claim 2 wherein the amount of water mixed with said copolymer is in excess of the amount required to saturate the copolymer with water.

4. The method of claim 3 wherein said data is in the form of a curve obtained by plotting the melt point against percent by weight vinyl acetate of each copolymer of said series.

* * * * *